(12) United States Patent
Millou et al.

(10) Patent No.: US 7,666,454 B2
(45) Date of Patent: Feb. 23, 2010

(54) **COSMETIC COMPOSITION COMPRISING AN ESSENTIAL OIL EXTRACTED FROM *HELICHRYSUM ITALICUM***

(75) Inventors: Yves Millou, Valensole (FR); Katia Fontes, Meyrargues (FR); Cecile Tourel, Aix-en-Provence (FR)

(73) Assignee: L'Occitane (FR)

( * ) Notice: Subject to any disclaimer, the term of this patent is extended or adjusted under 35 U.S.C. 154(b) by 421 days.

(21) Appl. No.: 10/785,237

(22) Filed: Feb. 24, 2004

(65) Prior Publication Data

US 2004/0258783 A1    Dec. 23, 2004

Related U.S. Application Data

(63) Continuation of application No. PCT/FR02/02954, filed on Aug. 28, 2002.

(30) Foreign Application Priority Data

Aug. 29, 2001 (FR) .................. 01 11224

(51) Int. Cl.
  *A61K 36/28* (2006.01)
  *A61K 36/287* (2006.01)
(52) U.S. Cl. ................. 424/764; 424/401; 424/725; 424/778
(58) Field of Classification Search ................. 424/725, 424/764, 778, 401
See application file for complete search history.

(56) References Cited

U.S. PATENT DOCUMENTS 5,785,972 A    7/1998  Tyler

2002/0119954 A1 * 8/2002 Afriat et al. .................... 514/63

FOREIGN PATENT DOCUMENTS

| FR | 2774585 A1 * | 8/1999 |
| FR | 2 819 718 | 7/2002 |
| JP | 2001-302532 A | 10/2001 |
| WO | WO 98/05294 | 2/1998 |
| WO | WO 00/35577 | 6/2000 |

OTHER PUBLICATIONS

Pullaiah, T., Encyclopaedia of World Medicinal Plants, 2006, Regency Publications, vol. 3, p. 1068.*
Spina, J. "Composition for arresting hair loss, for treating dandruff and itchy scalp and for promoting hair re-growth", Aug. 13, 1999, Derwent-Acc-No. 1999-471299, English abstract of FR 2774585 A1.*
Chirkina, N. N., etal. *Antimicrobial properties of essential oils from everlasting flowers*, Chemical Abstracts, vol. 81, No. 9, Sep. 2, 1974, Abstract No. 45837s, p. 75, XP002197962, Biol. Nauki, vol. 17, No. 1, 1974, pp. 86-89.
Maffei Facino, R. et al., *Phytochemical characterization and radical scavenger activity of flavonoids from Helichrysum italicum G. Don*, Chemical Abstracts, vol. 115, No. 5, 1991, Abstract No. 41926t, Pharmacoligical Research, vol. 22, No. 6, 1990, pp. 709-721.
Amrita: "*Helichrysum italicum*", Amrita, 'Online! 1999, XP002224497, p. 1, paragraph 7.
Satta M., et al., *Analysis of the essential oil of Helichrysum italicum*, Chemical Abstracts, vol. 132, No. 17, Apr. 24, 2000, Abstract No. 219523a, p. 399, XP002197960, Journal of Essential Oil Research, Vol. 11, No. 6, 1999, pp. 711-715.

* cited by examiner

*Primary Examiner*—Gina C Yu
(74) *Attorney, Agent, or Firm*—DLA Piper LLP (US)

(57) ABSTRACT

An antiwrinkle cosmetic composition comprising a substantially purified essential oil extracted from flower tops of *Helichrysum italicum* and a method of treating wrinkles in skin comprising applying on the skin an effective quantity of a cosmetic composition.

16 Claims, 5 Drawing Sheets

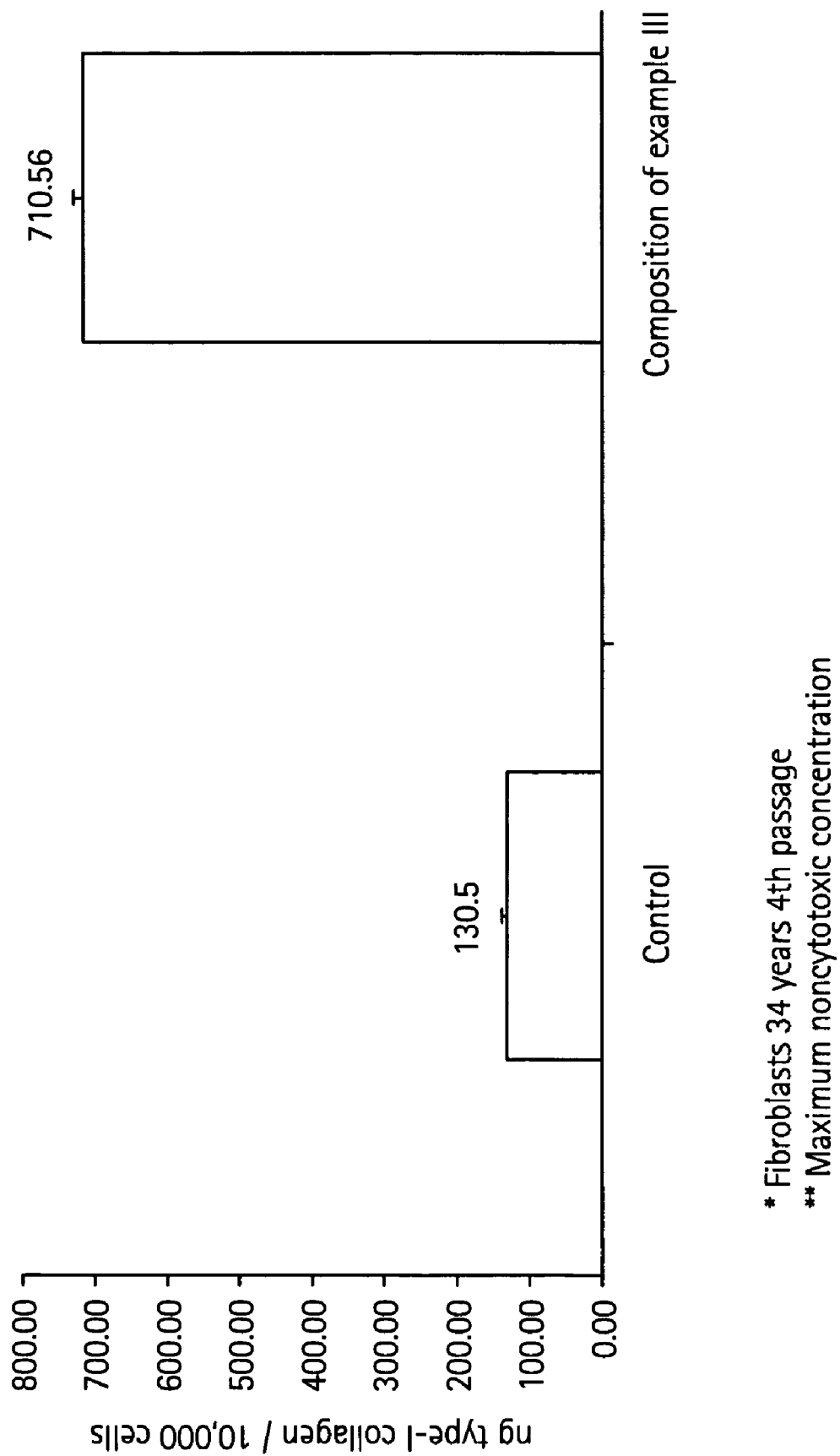

Culture at the initial stage (day 1)

Endothelial cells forming small islets

Culture on day 6

Development of tubules

Solvent control

Composition example III 0.005%

Suramin

Composition example III 0.01%

VEGF

Composition example III 0.05%

| Conditions | Modulation factors of the length of the tubules (% of the control or solvent) |
|---|---|
| Suramin | -49% |
| VEGF | +54% |
| Composition example III 0.005% | +6% (NS) |
| Composition example III 0.01 % | +11% (NS) |
| Composition example III 0.05 % | +6% (NS) |

| Conditions | Modulation factors of the number of junctions in relation to the control / solvent |
|---|---|
| Suramin | -5.7 |
| VEGF | +1.7 |
| Composition example III 0.005 % | +1.5 |
| Composition example III 0.01 % | +2 |
| Composition example III 0.05 % | +1.6 |

COSMETIC COMPOSITION COMPRISING AN ESSENTIAL OIL EXTRACTED FROM HELICHRYSUM ITALICUM

RELATED APPLICATION

This is a continuation of International Application No. PCT/FR02/02954, with an international filing date of Aug. 28, 2002 (WO 03/018730, published Mar. 6, 2003), which is based on French Patent Application No. 01/11224, filed Aug. 29, 2001.

FIELD OF THE INVENTION

This invention relates to an essential oil extracted from *Helichrysum italicum*, its preparation, as well as cosmetic and dermatological compositions containing it.

BACKGROUND

There are approximately 500 *Helichrysum* species. They are very polymorphous and difficult to distinguish from each other. Knowledge about them remains very limited and extraction of the essence by distillation is rarely performed.

Nevertheless, there has already been reported in the prior art the preparation of an essential oil of *Helichrysum italicum* comprising neryl acetate (28.9%) (Satta M. et al., CAS, Vol. 132, No. 17, Apr. 24, 2000).

Isolation of flavonoids from *Helichrysum italicum* and their protective activity in relation to the degeneration process of the skin has also been described (Maffei Facino R. et al., CAS, Vol. 115, No. 1991). However, the flavonoids are not related in any way to neryl acetate.

Finally, it has been reported that the essential oil of *Helichrysum italicum* exhibits antimicrobial properties (Chirkina N. N. et al., CAS, Vol. 81, No. 9, Sep. 2, 1994) and can be used in antiseptic compositions to promote cicatrization (U.S. Pat. No. 5,785,972).

SUMMARY OF THE INVENTION

This invention relates to an antiwrinkle cosmetic composition including a substantially purified essential oil extracted from flower tops of *Helichrysum italicum*.

This invention also relates to a method of treating wrinkles in skin including applying on the skin an effective quantity of a cosmetic composition.

This invention further relates to a method of preventing wrinkles in skin including applying on the skin an effective quantity of a cosmetic composition.

BRIEF DESCRIPTION OF THE DRAWINGS

FIG. 1 is a graph comparing a control against a composition for the face.

DETAILED DESCRIPTION

Figure 2A:
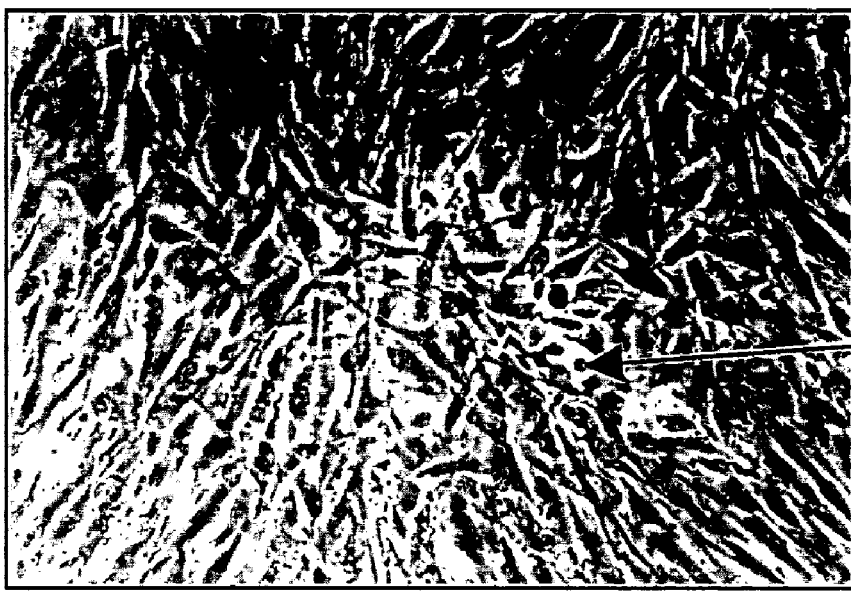
FIG. 2*a* is a photograph of a depiction of culture cells on day 1 of an experiment.

We performed research pertaining to the preparation of the essential oil extracted by hydrodistillation or by means of an extraction fluid preferably at or close to the supercritical state from the plant material of the flower tops of a plant from the Asterasceae family: *Helichrysum italicum* variety serotinum, also named *Helichrysum angustifolium* D.C.

We discovered remarkable cosmetic and dermatological properties of an essential oil from *Helichrysum italicum*. The neryl acetate, which is present in a high percentage in the essential oil of *Helichrysum italicum*, provides it with very particular properties in these fields:

very high antiradical activity;

very significant multiplication of the production of collagen I, on the order of sixfold;

augmentation of the production of VEGF on the order of twofold;

increase in cellular exchanges;

activation of the cutaneous microcirculation which as corollary facilitates the elimination of waste products, and thus the revitalization of the cells and stimulation of the cutaneous biology;

decongestant and protective properties reinforcing the equilibriums and defenses at the level of the skin; and antiseptic and dermal purification action contributing to the rehabilitation of the cellular environment.

Thus, we discovered a cosmetic composition, particularly an antiwrinkle, antiaging or hydrating composition, comprising an essential oil extracted from the flower tops of *Helichrysum italicum*, more particularly, of the variety serotinum also named *Helichrysum angustifolium* D.C. The composition according to the invention is most particularly intended for treatment of the face and body.

The composition of the invention is useful for the treatment of the skin: it has a most particular value for battling aging of the skin (antiaging) and notably for the treatment or prevention of wrinkles, and for hydrating the skin or protecting it from the damaging effects of the environment such as the sun (solar composition).

The essential oil is advantageously obtained by hydrodistillation or by means of an extraction fluid, at or close to the supercritical state.

The composition of the essential oil of *Helichrysum italicum* from Corsica is very original. Its principal constituent, neryl acetate, is present in a very high proportion, from about 40 to about 50% on average, and up to about 70% in the Balagne mountains in the northwestern part of Corsica. It should be noted that neryl acetate is present in a high proportion when the flower tops are distilled. This level falls to about 5% when the whole plant is distilled.

Most preferably, the invention pertains to the nontherapeutic use of the essential oil of *Helichrysum italicum* as defined above in a cosmetic composition for the treatment of the skin, particularly battling against wrinkles and/or hydrating the skin, and more generally battling the effects of aging.

More particularly, the invention pertains to the use of the essential oil of *Helichrysum italicum* as a polyvalent antiradical agent for a cosmetic or dermatological composition for the treatment of the skin, notably in battling wrinkles and/or in hydrating the skin, and more generally in battling the effects of aging.

We also discovered the capacity of this essential oil to increase the production of collagen I and VEGF which have proven to be particularly useful for battling wrinkles and more generally the aging of the skin.

As stated above, the essential oil, its use and the compositions containing it have remarkable properties for:

hydrating the skin;

increasing cellular exchanges;

activating the cutaneous microcirculation and thereby facilitating elimination of waste products and revitalizing the cells;

decongesting, protecting and thereby reinforcing the equilibriums and the defenses at the level of the skin; and rehabilitating the cellular environment.

The compositions according to the invention comprise an effective quantity of the oil to obtain the demonstrated antiradical as well as collagen I and VEGF promoting effects. This quantity represents from about 0.1 to about 5%, preferably from about 0.1 to about 2.1%, by weight of the oil in relation to the weight of the composition.

The cosmetic and dermatological compositions according to the invention can comprise other active ingredients such as (presented here as nonlimitative examples): natural perhydrosqualene, sucroesters, borage oil, oenothera oil, grapestone oil, vitamin A, vitamin E, allantoin and the like.

The cosmetic and dermatological compositions according to the invention generally also comprise one or more formulation agents, such as surface-active agents, preservatives, solubilizing agents, gelling agents, nonvegetable fatty additives, propylene glycol, sorbitol, glycerol, triethanolamine, perfume bases and water in a sufficient quantity for 100.

The compositions according to the invention can be produced in any form known in the art of cosmetics and dermatology, such as, for example, a cream, a milk, a lotion, a gel or a mask, without any particular pharmaceutical restriction other than that of compatibility with the oil of the invention and for application to the skin.

The oil according to the invention can be in free form or enclosed in nanospheres providing delayed release to create a persistent effect. We can cite spherulites or those described in WO 00/35577 as examples of such nanospheres.

Thus, one aspect of the invention is a method of cosmetic treatment comprising applying to the skin an adequate and effective quantity of the above composition.

Other advantages and characteristics of the invention will become apparent from the examples below pertaining to the preparation and properties of the essential oil of *Helichrysum angustifolium* D.C.

EXAMPLES

Preparation of the Essential Oil of *Helichrysum angustifolium* D.C.

The extraction of the essential oil for this type of plant is performed with a steam generator in which the vaporized fluid is conducted by a pipe into the bottom of an extraction chamber in which the plant materials are enclosed. This installation is connected to a pressure regulation control device.

The extraction fluids are conducted into a cooling coil. The final separation of the extraction fluids and the components of the essential oils is performed at atmospheric pressure by difference in density. This technique is known.

Antiradical Power of the Essential Oil of *Helichrysum angustifolium* D.C.

The hydroxyl radical is a very reactive molecule, the production of which is activated by the different stresses to which the skin is subjected (pollution, UV, temperature changes and the like). This radical is responsible for numerous waste products in the cell and especially the degradation of the membranes by the phenomenon of lipid peroxidation. This method makes it possible to test the protective action of the product on liposomes (membrane analogs) subjected to an attack by hydroxyl radicals (OH—).

The action of free radicals on the polyunsaturated fatty acids of the membranes is a peroxidation which leads to the formation of conjugated dienes absorbing at 233 nm. The activity of the antioxidants is, therefore, determined by their capacity to prevent peroxidation of polyunsaturated fatty acids contained in liposomes (in vitro model that comes closest to the in vivo reality). This peroxidation is characterized by an absorption peak at 233 nm. The method and the protocol employed are known.

We found that the product essential oil of *Helichrysum italicum* inhibits lipid peroxidation by 82%+2% under the experimental conditions. This result is remarkably positive. Tested under the same operating conditions, an essential oil of lavender inhibited lipid peroxidation by 19%+2%.

This antiradical activity is essential in the battle against accelerated aging. The preferential targets of the free radicals are the lipids of the cell membranes. By attacking them, they disturb the meticulous organization. The membrane loses its fluidity and its cohesion. In the long term, it breaks up and can no longer fulfill its role as a protective barrier. The connecting tissue, constituted essentially of collagen, is also affected. This accelerates the aging process.

Two simple concepts should be kept in mind to better comprehend the phenomenon of accelerated aging:

an atom is an electrically neutral set of elements in equilibrium; and a free radical is an atom possessing a single electron which confers upon the radical a very high degree of reactivity in the search for another electron to restore a stable state.

In the search for a stable state, the free radicals are very active and induce noteworthy reactional modifications within the cell, modifications that can reach the DNA and the amino acids. They depolymerize the glycoprotein constituents of the fundamental substance such as hyaluronic acid.

The free radicals have a profoundly negative impact on the lipids, proteins and other components of the cell membrane. The attacks on the cell membranes, due to the peroxidation process, increase with age. Research studying the interference of the auto-oxidation of the brain and renal tissues of 24 animal species demonstrated the existence of a direct relation between the longevity of each species and the potential for the production of peroxides and free radicals. These studies also showed the importance of antioxidants in the longevity process. In fact, the animal or plant cell protects itself against oxidation agents by means of enzyme systems and natural antioxidants.

We found the essential oil of *Helichrysum italicum* to be an effective natural antioxidant.

A Composition for the Face

The following formulation of a product for the face containing 0.7% of essential oil of *Helichrysum italicum* was prepared to demonstrate antiwrinkle activity:

| | |
|---|---|
| Essential oil of *Helichrysum italicum* | 0.7 |
| Grapestone oil | 80.02 |
| Borage oil | 1 |
| Natural perhydrosqualene | 18 |
| Natural vitamin E | 0.2 |
| Rosemary extract | 0.05 |
| Geranium essential oil | 0.03 |

The study of the cutaneous relief was performed by the prints method. The test involved 20 volunteer subjects. Application of cosmetics or other topical products was discontinued 48 hours prior to the beginning of the experiment. The product was applied each morning for four weeks and the following parameters were evaluated:

Total Wrinkled Surface:

This parameter provides information on the total surface area of the wrinkles (mm$^2$)

Average at Time 0=4.571 mm$^2$

Average at Time 4 weeks=2.843 mm$^2$

Thus, a decrease of 37.8%.

Number of Wrinkles:

Average at Time 0=61.3

Average at Time 4 weeks=52.7

Thus, a decrease of 14%.

Average Depth of the Wrinkles (Taking into Account the Number of Wrinkles That had Disappeared after Treatment):

A decrease of 19.8%.

The results for these three parameters were very satisfactory and demonstrated the remarkable antiwrinkle property of the compositions according to the invention. Biomechanical properties of the skin with the composition for the face Twenty users were recruited for a daily application over four weeks.

Result: UR/UB=R5: firmness under stress: +14.7%+0.11.

The composition for the face above provides a good cutaneous firmness. Evaluation of the hydration by the prints method with the composition for the face Twenty users were recruited for a daily application over four weeks.

Result: The parameter AR=Average roughness decreased by 8.9%, which was manifested by cutaneous smoothness, i.e., a hydrating effect.

Encapsulation of *Helichrysum italicum* Essential Oil in Nanospheres

The oil was incorporated in nanospheres to optimize the activity of *Helichrysum italicum* essential oil. This method has the advantage of increasing the bioavailability of the active ingredients. The controlled release of the active ingredients augments the chronoavailability at the level of the cutaneous cells. The *Helichrysum italicum* essential oil was encapsulated in spherulites. Spherulites are multilamellar vesicles of approximately one micron which imitate the structure of an onion. The hundreds of membranes of which they are composed form an alternation of bilayers containing sucroester and an optimized level of essential oils.

Because of the slow and controlled release of the active ingredient, the spherulites makes it possible to reduce the percentage of essential oil while still retaining the same level of efficacy. The benefit is a very improved tolerance, hypoallergenicity and an activation of the microcirculation.

The facial cream formulation below was prepared:

| | |
|---|---|
| *Helichrysum italicum* spherulites | 2 |
| Fatty alcohol | 4 |
| Grapestone oil | 5 |
| Glycerol | 5 |
| Rosemary extract | 0.05 |
| Vitamin A | 0.2 |
| Natural vitamin E | 0.2 |
| Surface-active agents | 5 |
| Preservatives | 0.9 |
| Perfumed based | 0.5 |
| Demineralized water | Q.S. |

A study of the cutaneous relief was performed using the prints method. The experiment involved 20 volunteer subjects. Applications of cosmetics or other topical products were suspended 48 hours prior to the beginning of the experiment. The product was applied every morning over four weeks and the following parameters were evaluated:

Total Wrinkled Surface:

This parameter provides information on the total surface area of the wrinkles (mm$^2$)

Average at Time 0=4.571 mm$^2$

Average at Time 4 weeks=2.843 mm$^2$

Thus, a decrease of 37.8%.

Number of Wrinkles:

Average at Time 0=61.3

Average at Time 4 weeks=52.7

Thus, a decrease of 14%

Average Depth of the Wrinkles (Taking into Account the Number of Wrinkles that Had Disappeared after Treatment):

A decrease of 19.8%.

The results for these three parameters were very satisfactory and demonstrated the remarkable antiwrinkle property of the compositions according to the invention.

Study of the Biomechanical Properties of the Skin with the Composition in Nanospheres Twenty users were recruited for daily administration over four weeks.

Result: UR/UB=R5: firmness under stress: +14.7%+0.11.

The composition of the composition in nanosphere above provides good cutaneous firmness.

Study of the Biomechanical Properties of the Skin with the Composition in Nanospheres Twenty users were recruited for daily application during four weeks.

Result: The parameter AR=Average roughness decreased by 8.9%, which was manifested by cutaneous smoothness, i.e., a hydrating effect.

Study of the Effect of the Composition of Example III on the Synthesis of Type 1 Collagen Introduction The fibers of the dermis: The fibers of the dermis comprise collagen fibers and elastic fibers. Quantitatively, they represent the more important structural proteins of the dermis, i.e., respectively 75 and 5% of their dry weight. Their relative proportion and their arrangement differ according to the superficial or deep regions of the dermis.

The fibroblasts: The fibroblasts are responsible for the synthesis and maintenance of the extracellular material. These are the cells of mesenchymal origin which synthesize collagen, elastin, the fundamental substance and the structural glycoproteins.

The collagen fibers: The collagens form a very large family. They are molecules with an extracellular matrix composed of three polypeptide chains bearing the repetition of three amino acids: -Gly-X-Y, in which X and Y are often prolines or hydroxyprolines. The collagen fibers of the dermis are constituted respectively of collagen I and collagen III, around an axis composed of collagen V. These collagens belong to the group of fibrillary collagens. In the adult, collagen I is on average six times more abundant than collagen III.

Collagens and aging: The collagen I/collagen III ratio decreases over the course of aging. There can be seen an exponential increase in chemical bridges between the collagen fibers due to Maillard's nonenzymatic glycation reaction. This chemical bridging of the collagen results in a rigidification of the fibers. Its degradation and its renewal are thereby slowed down.

Modification of the fibroblasts: The fibroblast is a key cell of the connective tissue which intervenes in the formation and stabilization of the elastic fibers, but also in their dystrophy and their lysis. Upon aging, the fibroblast decreases its activity and this cell at rest is called a fibrocyte. It becomes globular with diminution of its cytoplasm and rarefaction of its endoplasmic reticulum the vesicles of which are very dispersed. This cell is no longer in contact with the collagen.

Principle of the Study

The modification promoting the loss of elasticity and firmness of the skin due to the disorganization and rarefaction of the collagen was studied to demonstrate the efficacy of the compositions of the invention.

Thus, the activity of the composition on the secretion of collagen I in the culture medium by the fibroblasts was evaluated. The experimental model employed consisted of a culture of normal human fibroblasts up to confluence. These cells were incubated with the composition for the face at 0.05% (concentration determined to be noncytotoxic for the cells in the MTT test). Using the enzyme-linked immunosorbent assay (ELISA) method, which has the advantage of being easy to perform, sensitive and specific, we determined quantitatively the type-1 collagen in the culture medium.

In a first step, the fibroblast cultures were established by the explant method from samples of healthy Caucasian skin (abdominal plasty). The fibroblasts were cultured until confluence at 37° in a minimum essential medium (MEM) containing 2 mM of L-glutamine and 10% fetal calf serum in a moisture-saturated atmosphere with 5% of $CO_2$. Then, after detachment with a buffered pH 7.2 isotonic solution of trypsin at 0.1% and EDTA 0.02%, the cells were distributed on 96-well microplates (Falcon) at the rate of $10^4$ cells per well in the previously specified medium. After 24 hours, this medium was replaced for an incubation of 48 hours in the same medium without serum containing 0.15 mM of sodium ascorbate (incubation medium) with or without the complex of active ingredients to be tested.

A type of fibroblast was selected for the study, being fibroblasts of the $4^{th}$ passage or re-inoculation of culture, representing cells having normal characteristics (fusiform or star-shaped appearance, good metabolic activity, good spreading capacity and the like).

Quantitative determination of the collagen: The quantity of type-I collagen secreted in the medium after incubation with or without the active complex was determined using an ELISA test. This method detects certain nonradioactive molecules at very low levels. A direct method was selected, consisting of the absorption of the antigen (type-I collagen) in a solid phase (plastic of a microtitration plate designed for ELISA).

The incubation medium was collected and transferred into the wells of a microtitration plate. Incubation for 24 hours at +4° C. caused adhesion of the collagen to the plastic. The plate was then rinsed in phosphate buffer saline (PBS). After 24 hours of incubation at +4° C. with serum albumin (2% in PBS) to avoid nonspecific antibody-plastic binding, murine anticollagen I antibodies (Sigma) (dilution 1:2000) conjugated to an alkaline phosphatase (2 hours at ambient temperature), which in the presence of paranitrophenyl phosphate would produce paranitrophenol absorbing at 405 nm (1 hour at ambient temperature). The optical densities obtained were converted into ng of collagen using a calibration curve established under the same experimental conditions with type-I collagen.

Results (FIG. 1)

The composition for the face used at 0.05% in the culture medium enabled the fibroblasts to synthesize up to six times more type-I collagen compared to the control (culture medium alone).

The composition for the face initiated and stimulated synthesis programs of one of the predominant components of the extracellular matrix of the dermis, type-I collagen. It is thus an excellent booster of the reorganization of the collagen fibers. Thus, the composition for the face improves the tonicity of the skin.

Study of the Angiogenic Capacity of the Composition or the Face

Angiogenesis is a fundamental process by which new blood vessels are formed. A large number of events are involved including:

proteolytic degradation of the extracellular matrix;
migration and proliferation of endothelial cells;
formation of a new extracellular matrix; and
formation of tubules and anastomoses of the neoformed vessels.

These actions depend on vascular endothelial growth factor (VEGF). VEGF is an angiogenic factor and a mitogen for endothelial cells. It is a chemotactic factor for the monocytes and osteoblasts. Growth factor of the vascular endothelium, which is a vascular proliferation factor of production of neovessels, enables revascularization.

In vitro experimental models take into account solely in an individualized manner the different components of the angiogenesis process by studying the proliferation of endothelial cells or their migration or capacity to associate together in tubules when they are in contact with proteins of the extracellular matrix. However, none of these models reflects the global impact of anglogenesis.

The in vitro model we used was the AngioKit (Biopredic—ref ZHA-1000—lot no. 25173T) which approaches a more global vision of angiogenesis. In this model, human endothelial cells are seeded in a specific medium in co-culture with another type of human cells. In the initial phase, the endothelial cells form small islets. They begin to proliferate and then enter into a migration phase which leads to formation of structures of filamentous tubule form in the matrix. At the end of 10 to 12 days, the connections established form a network of anastomosed tubules. The staining of the tubules is obtained by specific marking of the antigen of surface antigen CD31 (PECAM-1), which is expressed by the endothelial cells.

The test is validated by staining the tubules and verification of the inhibitory and activating action of two pharmacological compounds known to act on angiogenesis. The action on angiogenesis of the active ingredients tested was evaluated by quantitative image analysis.

The cells were cultured in 24-well plates in an incubator at 37° C. under a humid atmosphere containing 5% $CO_2$. On the first day of the experiment, the microscopic observation showed the cells in the initial growth stage with a few small islets of endothelial cells (photograph of FIG. 2).

The specific culture medium was eliminated and the cells were placed under different experimental conditions:

Control: culture medium;

Negative control: suramin, agent inhibiting formation of tubules—final concentration: 20 µM;

Positive control: VEGF, activating agent of angiogenesis— final concentration: 2 ng/ml;

Composition for the face: Since this composition of essential oils is not miscible in the culture medium, it was dissolved in absolute ethanol and tested at three concentrations (the non-cytotoxic character of which had been verified in advance by 24-hour contact with normal human fibroblasts): 0.005%-0.01%-0.05% (v/v); and Solvent control: since ethanol could have effects on angiogenesis, it was tested at the final concentration required for dissolving the essential oils composition: 0.1% (v/v).

Figure 2B:
FIG. 2*b* is a photograph of a culture of cells on day 6 of the experiment as set forth with respect to FIG. 2*a*.
Figure 3A:
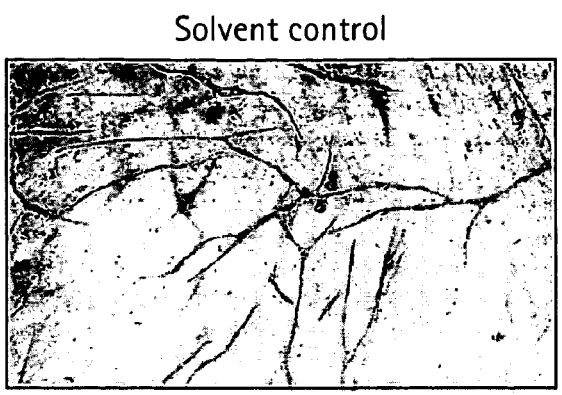
FIGS. 3A-F are images taken on the tenth day of the experiment referred to in FIGS. 2*a* and *b* of the solvent control, composition for the face 0.005%, suramin, composition for the face 0.01%, VEGF, and composition for the face 0.05% concentration, respectively.
Figure 3B:
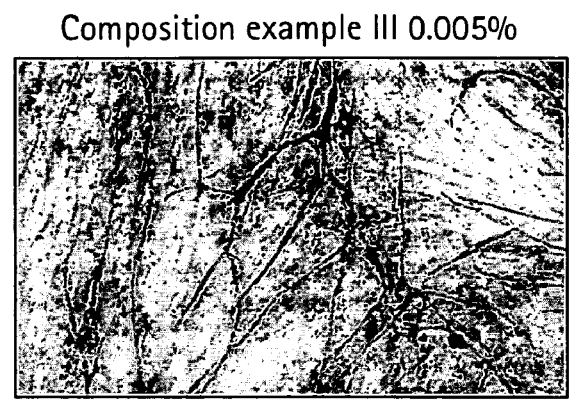
Figure 3C:
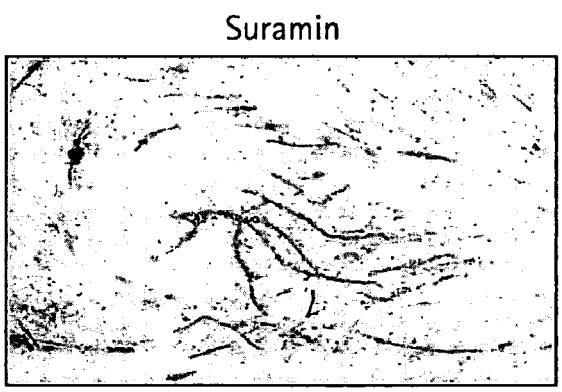
Figure 3D:
Figure 3E:
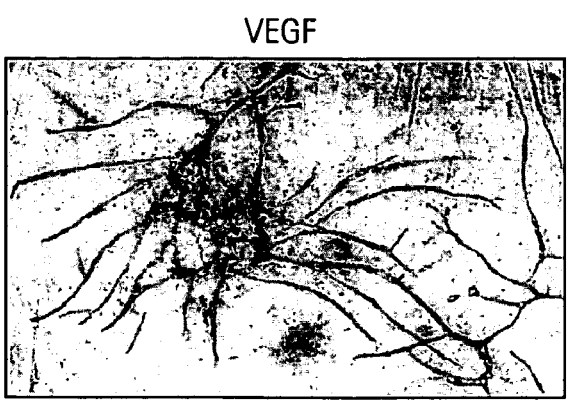
Figure 3F:

Each condition was implemented in duplicate. Microscopic observation of the cells was performed daily to monitor formation of tubules as shown in the photograph of FIG. 2.

The media were eliminated and the conditions were renewed on the $3^{rd}$, $6^{th}$ and $9^{th}$ day of the experiment. On the $10^{th}$ day, the cells were fixed and stained: after rinsing in the PBS buffer, the cells were fixed in a 70% ethanol solution cooled at −20° C. for 30 minutes. The cells were then incubated for 1 hour at 37° C. with the human anti-CD-31 ZIS-3090 antibody (TCS CellWorks). After washing, a second incubation of one hour at 37° C. was performed with a murine anti-IgG antibody conjugated with alkaline phosphatase. After rinsing, addition of BCIP/NBT substrate induced dark violet coloration of the tubules after incubation for 10 to 15 minutes.

Evaluation of the angiogenic power of the compound tested was quantified by image analysis (Olympus IX70 Auto Analysis System) by measuring the length of the tubules developed (in µm) and the number of junctions established within the anastomosed network. The results correspond to the average values obtained by analyzing 8 images for each condition.

FIG. 3 presents for each condition an image taken on the tenth day of experimentation of the neoformed anastomosed tubular network after fixation and staining. Evaluation of the angiogenic power of the composition for the face was performed by analysis of two criteria: the length of the tubular network and the number of junctions present in this network.

Figure 4:
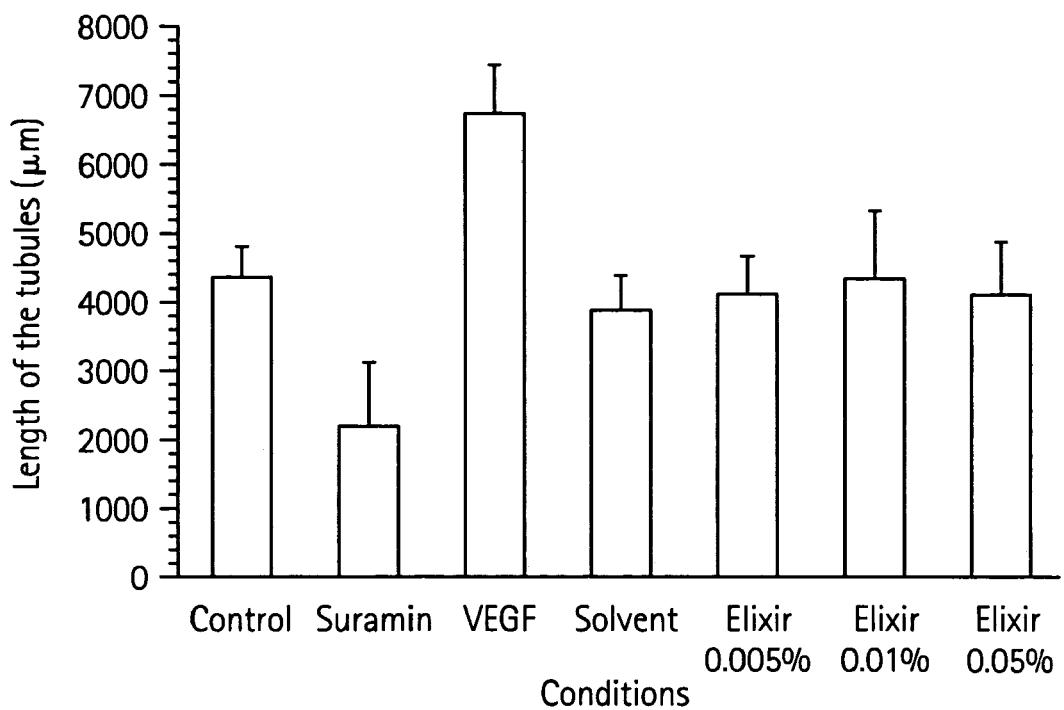
FIG. 4 is a graph of the conditions of the experiment referred to in FIGS. 2 and 3 versus length of tubules.

FIG. 4 presents the results of the quantitative analysis regarding the length of the neoformed tubules. The results obtained for the pharmacological compounds used as internal reference show in the presence of suramin an inhibition of 49% regarding the length of the tubular network compared to the control. VEGF had a stimulator effect of 54%. The solvent ethanol also interacted with the angiogenesis with an inhibitory effect of 11% compared to the control. The results obtained with the "Immortelle" elixir composition were calculated in relation to the solvent control.

The composition of the essential oil of *Helichrysum angustifolium* D.C. exhibited a slight stimulatory effect with regard to the length of the tubular network formed compared to the solvent condition. It was increased respectively by 6% at the concentration of 0.005%, by 11% at the concentration of 0.01% and by 6% at the concentration of 0.05%. These variations, however, were not statistically significant.

Figure 5:
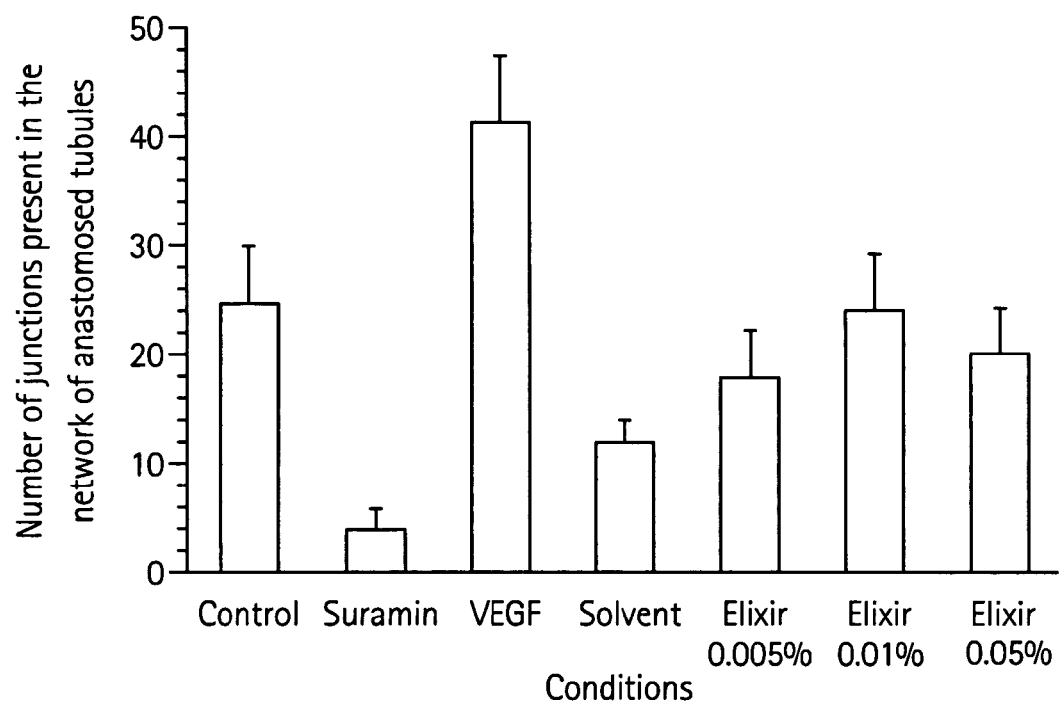
FIG. 5 is a graph of the conditions of the experiment referred to in FIGS. 2 and 3 versus number of junctions present in the network of tubules.

FIG. 5 presents the results of the quantitative analysis regarding the number of junctions established in the tubular network.

The number of junctions was diminished by a factor of 5.7 compared to the control in the presence of suramin. In contrast, with VEGF, the number of junctions was augmented by a factor of 1.7. The solvent ethanol also interacted by diminishing by a factor of 2 the number of junctions present in the network.

In the presence of the composition for the face, there can be seen for each of the concentrations a marked augmentation in the number of junctions compared to the solvent condition: augmentation by a factor of 1.5 at the concentration of 0.005%, augmentation by a factor of 2 at the concentration of 0.01% and augmentation by a factor of 1.6 at the concentration of 0.05%. It should be noted that these stimulatory effects had an intensity close to or even greater than those obtained with the positive reference (VEGF).

The composition for the face does not inhibit angiogenesis. To the contrary, it induces a stimulation by a factor of 2 of the number of anastomoses, an effect comparable to or even greater than that of VEGF. It thus exerts a stimulating role on the essential parameters of anglogenesis.

The invention claimed is:

1. An antiwrinkle cosmetic composition comprising about 0.1 to about 2.1% by weight of a purified essential oil extracted from the flower tops of *Helichrysum italicum* in relation to the weight of the composition, wherein the essential oil comprises 50 to 70% by weight of neryl acetate.

2. The cosmetic composition according to claim 1, adapted for application to the body or face.

3. The cosmetic composition according to claim 1, wherein the essential oil is obtained by hydrodistillation or by an extraction fluid at or close to the supercritical state.

4. The cosmetic composition according to claim 1, wherein the essential oil is enclosed in controlled-release nanospheres.

5. The cosmetic composition according to claim 1, further comprising a skin compatible carrier.

6. The cosmetic composition according to claim 1, further comprising an additional active ingredient selected from the group consisting of natural perhydrosqualene, sucroesters, borage oil, oenothera oil, grapestone oil, vitamin A, vitamin E and allantoin.

7. A method of cosmetic skin care selected from delaying appearance of skin aging effects, treating wrinkles, hydrating the skin, improving the firmness of the skin, reducing the appearance of wrinkles, and reducing depth of wrinkles, comprising topically applying to the skin of a person in need thereof a cosmetically effective amount of a composition comprising about 0.1 to about 2.1% by weight of a purified essential oil extracted from the flower tops of *Helichrysum italicum* in relation to the weight of the composition, wherein the essential oil comprises 50 to 70% by weight of neryl acetate.

8. The method of claim 7, wherein the composition is adapted for application to the body or face.

9. The method of claim 7, wherein the essential oil is obtained by hydrodistillation or by an extraction fluid at or close to supercritical state.

10. The method of claim 7, wherein the essential oil is enclosed in controlled-release nanospheres.

11. The method of claim 7, wherein the composition further comprises a skin compatible carrier.

12. The method of claim 7, wherein the composition further comprises an additional active ingredient selected from the group consisting of natural perhydrosqualene, sucroesters, borage oil, oenothera oil, grapestone oil, vitamin A, vitamin E and allantoin.

13. The method of claim 7, wherein the cosmetic skin care is treating wrinkles.

14. The method of claim 7, wherein the cosmetic skin care is hydrating of skin.

15. The method of claim 7, wherein the cosmetic skin care is reducing the appearance of wrinkles.

16. The antiwrinkle composition of claim 1, wherein the flower tops of *Helichrysum italicum* are from the mountains in the northwestern part of Corsica.

* * * * *